US008071556B2

(12) United States Patent
Khavinson et al.

(10) Patent No.: US 8,071,556 B2
(45) Date of Patent: Dec. 6, 2011

(54) PEPTIDE SUBSTANCE REVEALING A STRESS PROTECTIVE EFFECT, PHARMACEUTICAL COMPOSITION ON ITS BASE, AND THE METHOD OF ITS APPLICATION

(75) Inventors: Vladimir Khatskelevich Khavinson, St. Petersburg (RU); Evgeny Iosifovich Grigoriev, St. Petersburg (RU); Vladimir Victorovich Malinin, St. Petersburg (RU); Galina Anatolievna Ryzhak, St. Petersburg (RU)

(73) Assignee: Obschestvo S Ogranichennoi Otvetstevennostyu "Sia Peptides", Saint-Petersburg (RU)

( * ) Notice: Subject to any disclaimer, the term of this patent is extended or adjusted under 35 U.S.C. 154(b) by 342 days.

(21) Appl. No.: 12/298,430

(22) PCT Filed: Mar. 5, 2007

(86) PCT No.: PCT/RU2007/000105
§ 371 (c)(1),
(2), (4) Date: Oct. 24, 2008

(87) PCT Pub. No.: WO2007/136295
PCT Pub. Date: Nov. 29, 2007

(65) Prior Publication Data
US 2009/0105158 A1      Apr. 23, 2009

(30) Foreign Application Priority Data

May 23, 2006 (RU) ................ 2006117586

(51) Int. Cl.
*A61K 38/06* (2006.01)
*C07K 5/08* (2006.01)
(52) U.S. Cl. .......... 514/21.9; 530/300; 530/331
(58) Field of Classification Search .......... None
See application file for complete search history.

(56) References Cited

U.S. PATENT DOCUMENTS
6,727,227 B1    4/2004   Khavinson et al.

FOREIGN PATENT DOCUMENTS
| WO | WO 01/47950 A   | 7/2001  |
| WO | WO 2005/056580 A | 6/2005 |
| WO | WO 2006/001728 A | 1/2006 |
| WO | WO 2007/136294 A1 | 11/2007 |
| WO | WO 2007/139431 A1 | 12/2007 |
| WO | WO 2007/139435 A1 | 12/2007 |

OTHER PUBLICATIONS

Abiko T, Onodera I, Sekino H, "Characterization of an Acidic Tripeptide in Neurotoxic Dialysate," Chem. Pharm. Bull., 1980, 28(5): 1629-1633.*
Mileusnic, R. et al., "The Peptide Sequence Arg-Glu-Arg, Present in the Amyloid Precursor Protein, Protects Against Memory Loss Caused by Abeta and Acts as a Cognitive Enhancer" European Journal of Neuroscience, Apr. 2004, pp. 1933-1938, vol. 19, No. 7, Oxford University Press, Great Britain.
Khavinson, V Kh. et al., "Mechanisms Underlaying Geroprotective Effects of Peptides" Bulletin of Experimental Biology and Medicine, Jan. 2002, pp. 1-5, vol. 133, No. 1, Consultants Bureau, New York, NY.
Korkushko O. V. et al., "Geroprotective Effect of Epithalamine (Pineal Gland Peptide Preparation) in Elderly Subjects with Accelerated Aging" Bulletin of Experimental Biology and Medicine, Sep. 1, 2006, pp. 356-359, vol. 142, No. 3, Kluwer Academic Publishers, NE.
Wang Chao et al., "The Synthesis and Immunosuppressive Activities of Steroid-urotoxin Linkers" Bioorganic & Medicinal Chemistry, Aug. 15, 2004, pp. 4403-4421, vol. 12, No. 16.
Barabanova, S.V. et al., "[Parallel Analysis of C-Fos Protein and Interleukin-2 Expression in Hypothalmic Cells Under Different Influence]" Feb. 2007, pp. 150-160, vol. 92, No. 2, Rossi §SKII Fiziologicheski § Zhurnal Imeni I.M. Sechenova, Rossi §Skaia Akademiia Nauk, English abstract only.
Sibarov, D.A. et al., "Epitalon Influences Pineal Secretion in Stress-Exposed Rats in the Daytime" Neuroendocrinology Letters, 2002, pp. 452-454, vol. 23, No. 5-6, Sweden.
Ruiz-Alcaraz, Antonio J., et al., "Gonadins, a novel family of glutamyl-tripeptide amides present in the testis with activity in the hypophyseal-gonadal axis," *Regulatory Peptides*, vol. 129, 2005, pp. 93-101.

* cited by examiner

*Primary Examiner* — Julie Ha
(74) *Attorney, Agent, or Firm* — Leydig, Voit & Mayer, Ltd.

(57) ABSTRACT

Disclosed is a peptide glutamyl-aspartyl-glycine with general formula H-Glu-Asp-Gly-OH sequence 1 [SEQ ID NO:1], having a stress protective effect. Also disclosed is a pharmaceutical composition comprising the peptide and a pharmaceutically acceptable carrier. Also disclosed is a method of preventing or treating functional or stress induced disorders in a patient wherein the method involves administering an effective amount of the peptide to the patient.

14 Claims, 4 Drawing Sheets

Figure 1:
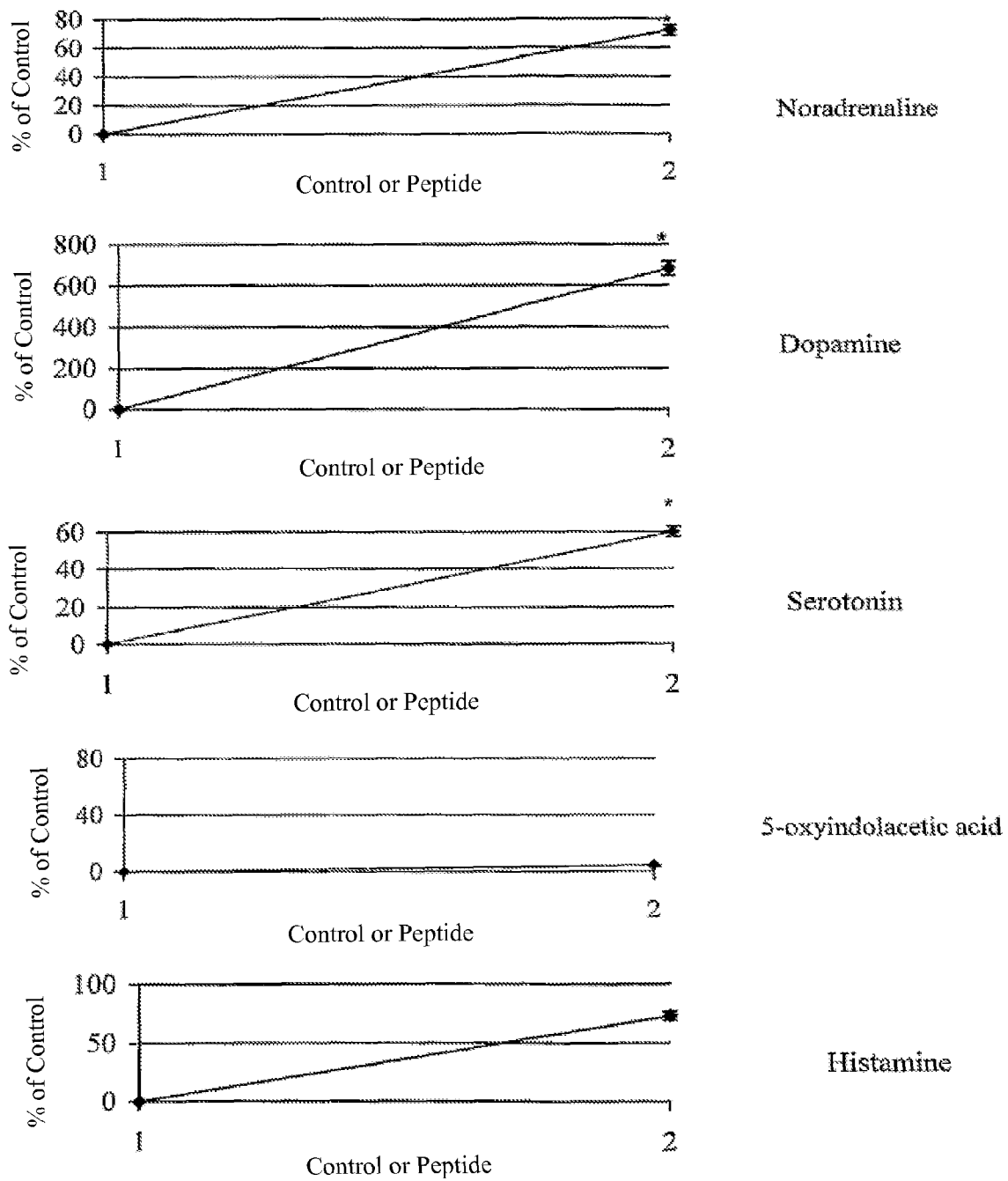

* - P<0.05 as compared to the control.

* - P<0,01 as compared to the control.

```
                       SEQUENCE LISTING

<160> NUMBER OF SEQ ID NOS: 1

<210> SEQ ID NO 1
<211> LENGTH: 3
<212> TYPE: PRT
<213> ORGANISM: Artificial
<220> FEATURE:
<223> OTHER INFORMATION: H-Glu-Asp-Gly-OH reveals a stress protective
      effect by regulating the content of biogen amines in the brain
      cortex and blood, by influencing c-fos gene expression in
      different brain structures and reducing the activity of
      encephalinases in the blood

<400> SEQUENCE: 1

Glu Asp Gly
1
```

PEPTIDE SUBSTANCE REVEALING A STRESS PROTECTIVE EFFECT, PHARMACEUTICAL COMPOSITION ON ITS BASE, AND THE METHOD OF ITS APPLICATION

The invention is related to the medicinal means of prevention and treatment of functional or stress induced disorders caused by extreme impacts and may be used as a medication revealing a stress protective effect.

It is known, that stress is a characteristic feature of the modern life. Stress has several aspects, of which the following are essential: adaptive reaction of the organism, insufficient adaptive reaction, pathologically dependent adaptive reaction to stress, premature aging of the organism, induced by nervous, mental and metabolic exhaustion.

No medications capable of effectively preventing and treating all aspects of stress were found in the prior art.

Depending on the clinical manifestations of stress, such preparations as tranquilizers, antidepressants, beta-adrenergic receptor blockers, sedative and hypnotic means, as well as herbal adaptogens are used.

These medications have a drawback, which consists in their being suitable only for symptomatic treatment, as well as their tendency to change anti-stress reactions of organism adaptation and can produce negative side effects.

There are known compositions including amino acids with vitamins or without them, or based on glutamates (RO Patent No. 76141), or on cysteine (RO Patent No. 74505), arginine (FR Patent No. 2494113), or compositions, which together with the mentioned above amino acids include: glycine, lysine, tyrosine, ornitine, hystine (FR Patent No. 5937M, RO Patent No. 76044).

Non-specific activity of said compositions, as well as their incapability to slow down organism aging can be also considered to be a disadvantage.

The above mentioned reasons provide for the necessity of designing new medicinal means.

Peptide glutamyl-aspartyl-glycine with general formula H-Glu-Asp-Gly-OH (registration number RN-65007-24-8 in STN int. BD Registry Chemical abstract) is known in the prior art.

Experimental studies of peptide glutamyl-aspartyl-glycine with general formula H-Glu-Asp-Gly-OH revealed its previously unknown stress protective effect.

The claimed invention has set and resolved the task of obtaining the means of peptide nature, revealing a stress protective activity, of a pharmaceutical composition on its base and of a method of its application.

Technical result of the invention consists in a stress protective effect, revealed by peptide glutamyl-aspartyl-glycine with general formula, H-Glu-Asp-Gly-OH, as well as in its application for manufacturing a pharmaceutical composition, containing this peptide as its active base, such composition being intended for regulating the level of biogen amines in the brain cortex and blood serum, affecting c-fos gene expression in different brain structures and reducing enkephalinase activity in blood, thus exerting a stress protective effect.

The possibility of objective attaining of the technical result while using the claimed invention has been confirmed by reliable data indicated in the examples, containing the experimental data obtained in the studies performed in accordance with the methods, which are universally accepted in this field of knowledge, according to which experimental stress was induced in animals.

This invention is related to the peptide glutamyl-aspartyl-glycine with general formula H-Glu-Asp-Gly-OH sequence 1 [SEQ ID NO:1], revealing a stress protective effect.

There is proposed an application of peptide glutamyl-aspartyl-glycine with general formula H-Glu-Asp-Gly-OH sequence 1 [SEQ ID NO:1] for manufacturing a pharmaceutical composition, revealing a stress protective effect.

The next aspect of this invention is related to the pharmaceutical composition revealing a stress protective effect, characterized in that such composition contains an effective amount of peptide glutamyl-aspartyl-glycine with general formula H-Glu-Asp-Gly-OH sequence 1 [SEQ ID NO:1] as its active base, and a pharmaceutically acceptable carrier.

In this case such pharmaceutical composition exists in the form suitable for parenteral or intranasal administration.

The next aspect of this invention is related to a method of prevention and/or treatment of functional or stress induced disorders, caused by extreme impacts, such method consisting in the administration to a patient of a pharmaceutical composition, containing an effective amount of peptide glutamyl-aspartyl-glycine with general formula H-Glu-Asp-Gly-OH sequence 1 [SEQ ID NO:1] as its active base in the dose of 0.01-100 µg/kg of body weight at least once a day during a period necessary for attaining a therapeutic effect. In this case the pharmaceutical composition is administered parenterally or by intranasal infusion.

Peptide glutamyl-aspartyl-glycine with general formula H-Glu-Asp-Gly-OH is obtained using the classical method of peptide synthesis in solution.

Biological activity of said peptide was studied in intact animals, in experimental models of stress, using blood serum of healthy people, and in human volunteers exposed to an extreme impact in the form of reduced oxygen partial pressure.

The notion "pharmaceutical composition" implies such different medicinal forms containing the new peptide, which may find therapeutic application as a medication revealing a stress protective effect. To obtain pharmaceutical compositions according to this invention, an effective amount of peptide H-Glu-Asp-Gly-OH as the active base is mixed with a pharmaceutically acceptable carrier according to the methods of compounding, which are universally accepted in pharmaceutics.

The notion "effective amount" implies the use of such amount of the active base, which, according to its quantitative indices of activity and toxicity, as well as to the knowledge of a competent specialist, must be effective in the given medicinal form.

The carrier may have different forms, depending on the medicinal form of the substance, which is desirable for the administration to the organism.

For parenteral administration, the carrier usually includes physiological saline solution or sterile water, although other ingredients promoting stability or preserving sterility may also be added.

For intranasal administration, the carrier usually includes physiological saline solution or sterile water, although other ingredients may also be added.

The subject matter of the claimed invention is explained by figures and a table.

FIG. 1 displays (% of the control) the effect of peptide H-Glu-Asp-Gly-OH on the level of biogen amines in rat brain cortex (1—control; 2—peptide H-Glu-Asp-Gly-OH).

Figure 2:
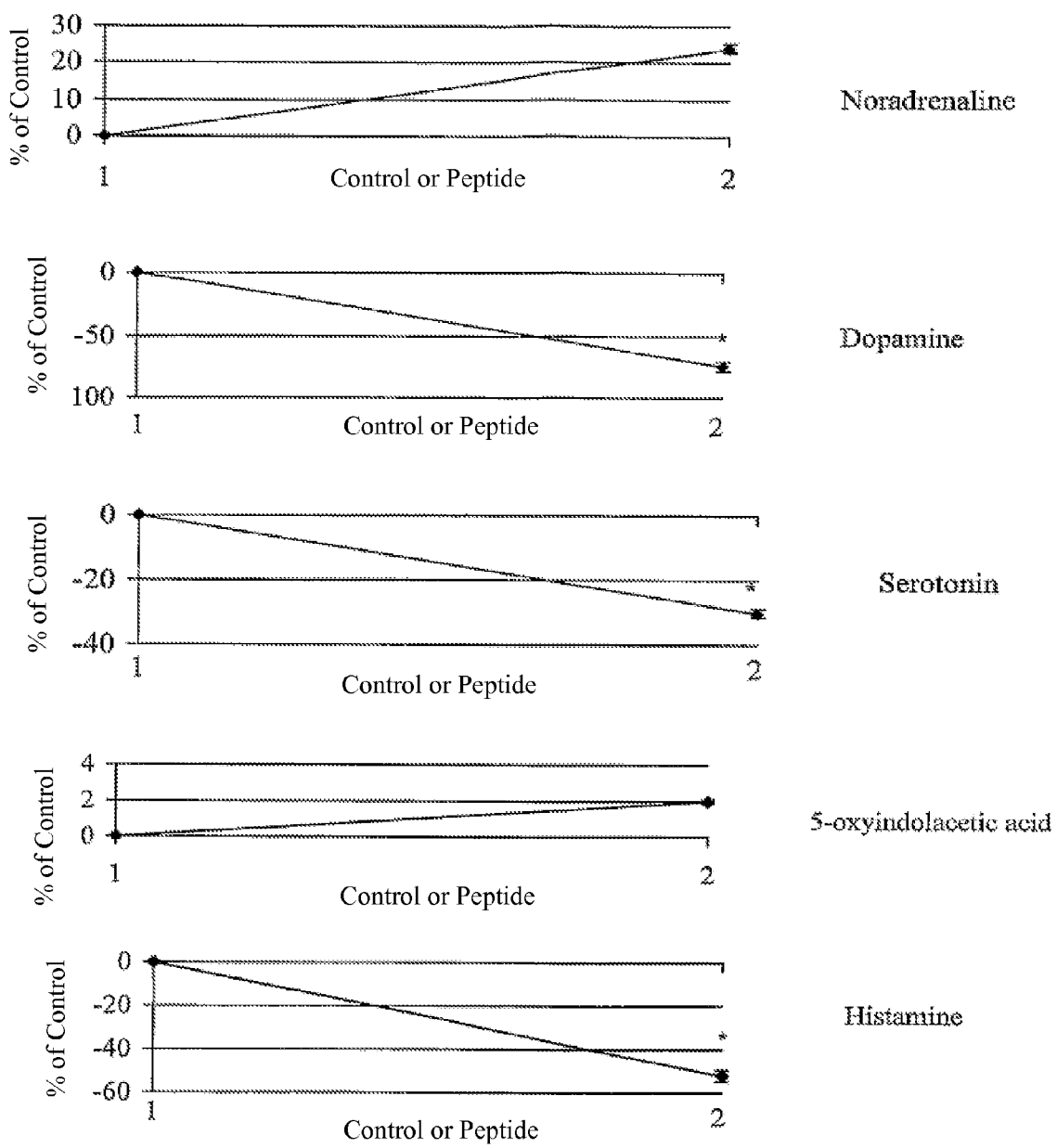

FIG. 2 displays (% of the control) the effect of peptide H-Glu-Asp-Gly-OH on the level of biogen amines in rat blood serum (1—control; 2—peptide H-Glu-Asp-Gly-OH).

Figure 3:
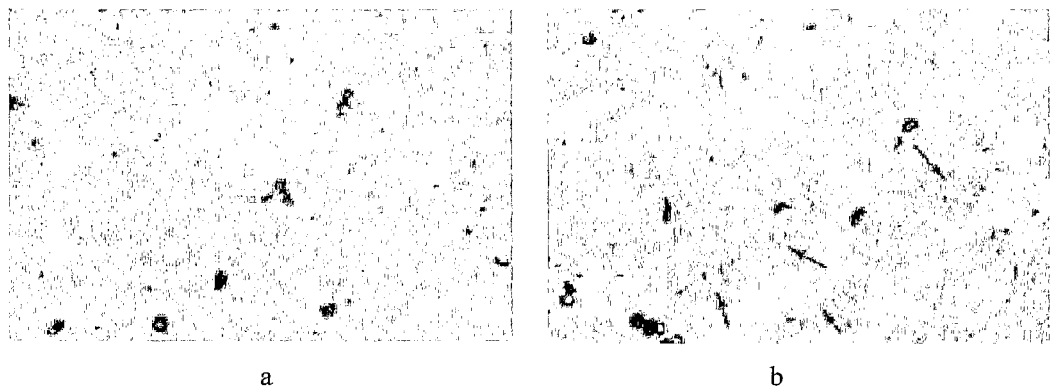

FIG. 3 displays the immunohistochemical identification of c-Fos protein content in pineal gland cells after osmotic stress (a—without peptide H-Glu-Asp-Gly-OH; b—after intranasal administration of peptide H-Glu-Asp-Gly-OH (clusters of c-Fos protein producing cells)).

Figure 4:
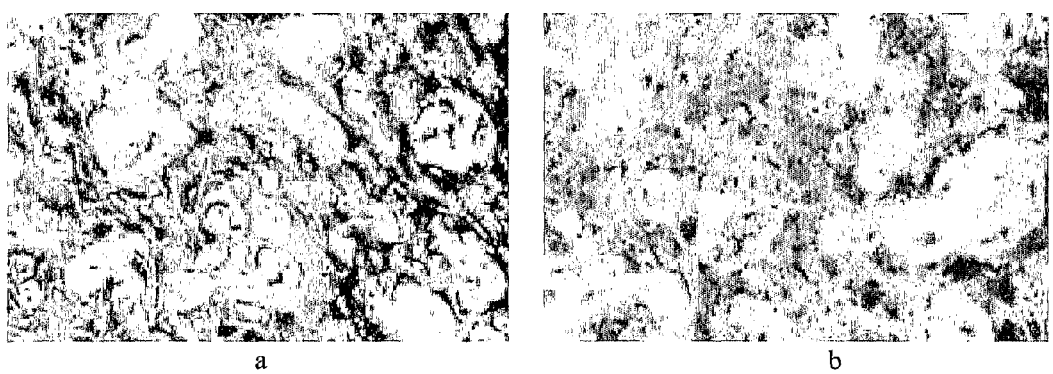

FIG. 4 displays the pineal gland parenchyma after osmotic stress (a—without peptide H-Glu-Asp-Gly-OH, b—after intranasal administration of peptide H-Glu-Asp-Gly-OH).

Figure 5:
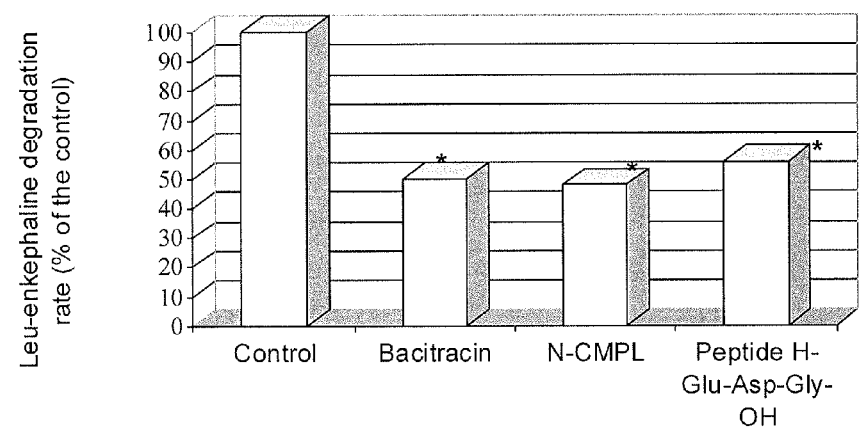

FIG. 5 displays the effect of peptide H-Glu-Asp-Gly-OH on enkephalinase activity in human blood serum.

Table displays the effect of peptide H-Glu-Asp-Gly-OH on morphological and biochemical indices of guinea pig peripheral blood in the study of toxicity.

The invention is illustrated by an example of synthesis of peptide glutamyl-aspatyl-glycine with general formula H-Glu-Asp-Gly-OH (Example 1), by examples confirming biological activity of the peptide (Examples 2, 3, 4, 5), by an example of study of toxicity (Example 6), as well as by an example of the results of clinical administration of the peptide, displaying its pharmaceutical properties and confirming the possibility of attaining a prophylactic and/or therapeutic effect (Example 7).

EXAMPLE 1

Synthesis of Peptide H-Glu-Asp-Gly-OH

1. Compound name: glutamyl-aspartyl-glycine
2. Structural formula: H-Glu-Asp-Gly-OH

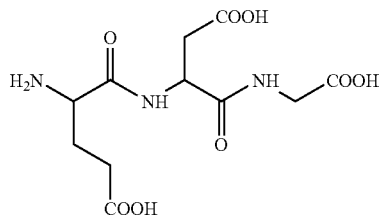

3. Molecular formula without ion pair: $C_{11}H_{17}N_3O_8$.
4. Molecular weight without ion pair: 319.27.
5. Ion pair: acetate.
6. Appearance: white amorphous powder without smell.
7. Method of synthesis: the peptide is obtained by a classical method of synthesis in a solution according to the following scheme:

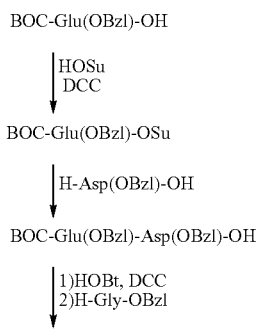

BOC—tert.butyloxycarbonyl group,
OSu—N-oxysuccinimide ester,
DCC—N,N'-dicyclohexylcarbodiimide,
OBzl—benzyl ester,
TFA—trifluoracetic acid,
HOBt—N-oxybenzotriazol Characteristics of the Ready Substance:
Base substance content: 97.93% (by HPLC, 220 nm),
TLC—individual, $R_f$=0.45 (acetonitrile-water 1:2),
Humidity content: 6%,
pH of 0.01% solution: 4.9
Specific rotary power: $[\alpha]_D^{22}$: $-31°$ (c=1, $H_2O$), "Polamat A", Carl Zeiss Jena.

EXAMPLE OF SYNTHESIS

1) BOC-Glu(OBzl)-OSu, N-oxysuccinimide ester of N-tert.butyloxycarbonyl-(γ-benzyl)glutamic acid (I)

N-tert.butyloxycarbonyl-(γ-benzyl)glutamic acid BOC-Glu(OBzl)-OH (33.7 g, 0.1 mole) is dissolved in 50 ml of N,N'-dimethylformamide, cooled down to $-10°$ C.; cooled (4-6° C.) solutions of N,N'-dicyclohexylcarbodiimide (23.0 g, 0.11 mole) in 30 ml N,N'dimethylformamide and N-hydroxysuccinimide (13.0 g, 0.11 mole) in 20 ml of N,N'-dimethylformamide are added while stirring. Reactive mixture is stirred for 12 hours on ice, and then for 24 hours at room temperature. Residual N,N'-dicyclohexylurea is filtered out, and the obtained solution of activated ester is used without extracting during the next stage.

2) BOC-Glu(OBzl)-Asp(OBzl)-OH, N-tert.butyloxycarbonile-(γ-benzyl)glutamyl-(β-benzyl)aspartate (II)

(β-benzyl)asparaginic acid H-Asp(OBzl)-OH (28.0 g, 0.12 mole) and 36 ml (0.12 mole) of triethylamine is suspended in 50 ml of N,N'-dimethylformamide and stirred for 1 hour. Then activated ester BOC-Glu(OBzl)-OSu (I) solution, obtained during the previous stage, is added in portions. The reactive mixture is stirred at room temperature for 48 hours. Then the mixture is acidated with 0.5 N sulphur acid up to pH 2-3 and extracted with ethyl acetate 4×50 ml. The extracts are put together and subsequently washed by 0.5 $NH_2SO_4$ 3×50 ml, water 2×50 ml, 5% $NaHCO_3$ solution 2×50 ml, water 2×50 ml, saturated NaCl solution 2×50 ml. The organic layer is dried over $Na_2SO_4$, the solvent is removed in vacuum, the residue is crystallized under hexane. 50 g of product is obtained (92%). $R_f$=0.34 (benzene-acetone 2:1).

3) BOC-Glu(OBzl)-Asp(OBzl)-Gly-OBzl (III), benzyl ether of N-tert.butyloxycarbonyl-(γ-benzyl)glutamyl-(β-benzyl)aspartyl glycine (III)

2.7 g (5 mmole) of dipeptide and 0.95 g (7 mmole) of oxybenzotriazol are dissolved in tetrahydrofuran (10 ml) and cooled down to $-10°$ C. 1.44 g (7 mmole) of dicyclohexylcarbodiimide are dissolved in 5 ml of tetrahydrofuran and cooled down to the same temperature. 3.4 g (10 mmole) of benzyl ester glycine tosilate are dissolved in 10 ml of tetrahydrofuran, 1.4 ml (10 mmole) of triethylamine is added to this solution and cooled down to the same temperature. In the process of cooling in the ice bath and intensive stirring the solutions of dipeptide with oxybenzotriazol and carbodiimide are united, then in 10 minutes glycine benzyl ester tosilate solution is added. The reactive mixture is stirred for 3 hours, cooled with ice, and then for 24 hours at room temperature. Fallout dicyclohexylurea is filtered out, the filtrate is removed in vacuum, residue is dissolved in ethyl acetate (100 ml). The solution is subsequently washed by 0.5 $NH_2SO_4$, water, 5% $NaHCO_3$ solution, water, dried over $Na_2SO_4$. Ethyl acetate is removed in vacuum, residue is crystallized in ethyl acetate/hexane system. Re-crystallization is performed from isopropanol, after which the mixture is dried in vacuum. 2.74 g of the product are obtained (85%). $R_f$=0.78 (benzene-acetone 1:1).

4) H-Glu-Asp-Gly-OH (IV), glutamyl-aspartyl-glycine

Protected tripeptide BOC-Glu(OBzl)-Asp(OBzl)-Gly-OBzl (III) (2.7 g) is dissolved in the mixture of methyl spirit—water (4:1) (50 ml) and hydrated over catalyst Pd/C (5%) for 4 hours. Catalyst is filtered out, solvent is removed in vacuum, residue is dried in vacuum over KOH and $P_2O_5$. Then the product is dissolved in 2 ml of chlorous methylene-trifluoracetic acid (5:1) mixture and held at room temperature for 2 hours. The fullness of deblockading reaction is controlled by TLC in acetonitrile-water system (1:3). Solvent is removed in vacuum, residue is dried in vacuum over KOH.

For the purpose of purification 300 mg of preparation is dissolved in 4 ml of 0.01% trifluoracetic acid and subjected to highly productive liquid chromatography on reverse phase column 50×250 mm Diasorb-130-C16T, 7 µm. Chromatograph Beckman System Gold, 126 Solvent Module, 168 Diode Array Detector Module. Conditions of chromatography: A: 0.1% TFA; B: MeCN/0.1% TFA, gradient B 0→50% in 100 minutes. Sample volume 5 ml, detection at 215 nm, scanning 190-600 nm, flow rate 10 ml/min. Main peak fraction is selected. The solvent is removed in vacuum at the temperature not higher than 40° C., removal is multiply (5 times) repeated with 10 ml of 10% acetic acid solution.

Finally the residue is dissolved in 20 ml of deionized water and lyophilized.

150 mg of purified substance in the form of amorphous white powder without smell is obtained.

5) Analysis of the Ready Substance

Base substance content is identified by HPLC on the column Phenomenex C18 LUNA 4.6×150 mm. A: 0.1% TFA, B: MeCN; grad.B 0-100% in 10 min. Flow rate 1 ml/min. Detection at 220 nm, scanning 190-600 nm, sample 20 µl. Base substance content 97.93%.

TLC: individual, $R_f$=0.45 (acetonitrile-water 1:2, Sorbfil plates, silicagel 8-12 µm, developing chlorine/benzidine).

Humidity content: 6% (gravimetrically, judging by weight loss by drying of 20 mg at 100° C.).

pH of 0.01% solution: 4.9 (potentiometrically).

Specific rotary power: $[\alpha]_D^{22}$: −31° (c=1, $H_2O$), "Polamat A", Carl Zeiss Jena.

EXAMPLE 2

Peptide H-Glu-Asp-Gly-OH Effect on the Level of Biogen Amines in Rat Brain Cortex and Blood Serum The study was performed on 27 white mongrel rats of both sexes with body weight of 300-320 g.

The animals were subjected to intraperitoneal injection of peptide H-Glu-Asp-Gly-OH in the dose of 2.5 µg/kg in 0.5 ml of sterile 0.9% NaCl solution daily for 5 days.

Control rats received sterile 0.9% NaCl solution in the same volume and by the same schedule.

Upon completion of peptide administration the animals were decapitated, and the content of noradrenaline, dopamine, 5-oxyindolacetic acid, serotonin and histamine was evaluated in the brain cortex and blood serum.

It was found, that the administration of the peptide to the animals contributed to significant changes in the level of biogen amines in the brain cortex and blood serum.

Thus, after the administration of peptide H-Glu-Asp-Gly-OH to rats a reliable increase in noradrenaline, dopamine and serotonin content was registered (FIG. 1).

At the same time there a decrease in dopamine, serotonin and histamine content was registered in the blood serum (FIG. 2).

Thus, the conducted study revealed that peptide H-Glu-Asp-Gly-OH exerts a modulating effect on the content of biogen amines in the brain cortex and the blood serum, which confirms the effect of the peptide on central and peripheral mechanisms of stress regulation.

EXAMPLE 3

Effect of peptide H-Glu-Asp-Gly-OH on c-fos Gene Expression in the Neurons of Rat Hypothalamic Paraventricular Nucleus Under Emotional Stress Emotional stress intensifies the expression of early genes in different brain structures. A well known marker of neural cells activation is c-Fos protein, a product of the immediate early response gene, which functions as a mediator between transcription change under the effect of a stimulus on one side and the process of informational signal realization into long-term phenotypical changes on the other side. Fos type proteins become active at different time after exposure to stimulus. So, c-fos mRNA expression starts in several minutes and reaches its maximum in 30-60 minutes. The maximum synthesis of c-fos protein is observed between the $1^{st}$ and the $3^{rd}$ hour, starting to decline in 4-6 hours after the exposure to the stimulus. C-fos gene expression in the brain of stress resistant animals and of those susceptible to stress impact is different. The most intensive c-fos gene expression in brain structures (cortex, tonsil, hypothalamus and truncus cerebri) was revealed in rats susceptible to emotional stress. In stress resistant rats in the same experimental conditions c-fos gene expression was registered only in infralimbus cortex and olfactory nuclei.

The effect of peptide H-Glu-Asp-Gly-OH was studied in the paraventicular nucleus of hypothalamus (PVH) in stress-resistant and stress-prone animals, as well as in rats exposed to emotional stress.

The experiments were conducted on 28 Wistar rats.

Behavior of the animals was preliminarily (for the purpose of identifying the extent of their resistance to emotional stress) estimated in the "open field" test. The effectiveness of peptide H-Glu-Asp-Gly-OH was studied on stress-resistant and stress-prone rats. Peptide H-Glu-Asp-Gly-OH was administered intraperitoneally in the doses of 0.1 and 0.01 µg per rat 7-10 days after the first "open field" test. One hour after the injection the rats were exposed to the 60 minutes emotional stress, which was modulated by motional restriction.

To identify the cells, containing Fos protein, which is a product of the early c-fos gene expression, an immunohystochemical investigation of brain section with automated counting of Fos-positive cells was performed. The peculiarities of c-fos gene induction were studied in the PVH.

These studies revealed that the number of Fos-positive cells in PVH of rats, which were identified as stress-resistant, was pronouncedly higher than in emotional stress susceptible animals. Both control groups (exposed to stress and not exposed to stress) showed the same results.

Peptide H-Glu-Asp-Gly-OH administration in the dose of 0.01 µg led to the increase in Fos-positive neural cells number in stress-resistant rats, both in not exposed and exposed to stress. Peptide H-Glu-Asp-Gly-OH in the dose of 0.1 µg on the contrary reduced the number of Fos-positive neural cells in PVH of both stress-resistant and stress-prone rats. Against the background of stress peptide H-Glu-Asp-Gly-OH in the dose of 0.1 µg increased number of Fos-positive neurons in stress-resistant animals.

Thus, dose-dependent stress protective effects of peptide H-Glu-Asp-Gly-OH, increasing c-fos gene expression, activating neurons and forming adaptation reactions, were revealed.

EXAMPLE 4

Effect of Peptide H-Glu-Asp-Gly-OH on the Level of c-Fos Protein in Rat Pineal Gland in Case of Osmotic Stress Along with hypothalamus-pituitary gland complex, the pineal gland is involved in the formation of multiple adaptive responses of the organism to stress impact. Stress augments pineal gland production of melatonin and of peptide substances capable of reducing the negative impact of oxidative, osmotic, psychic and other kinds of stress.

Pineal gland belongs to neurohemal organs not having a hematoencephalic barrier, and thus it is highly sensitive to high-molecular biologically active substances existing in the brain blood circulation, especially to peptides. Uniquely located olfactory system and chemical connection with both external environment and central nervous system enables the substances to non-invasively pervade into the brain blood circulation and into neurohemal organs. There is constant liquor diffusion via the subarachnoid space, along factor neurons and to the nasal submucosa and nasal lymph system.

Effect of intranasally administered H-Glu-Asp-Gly-OH peptide on c-Fos protein content in stress-affected rat pineal gland was studied. Immunohistochemical study of c-Fos protein content was performed in two groups of rats—intact and subjected to 48-hour osmotic stress. The latter were intranasally administered with peptide H-Glu-Asp-Gly-OH in the dose of 0.5 µg per animal in 0.1 ml of sterile physiological 0.9% NaCl solution (last infusion was performed 2 hours before taking the material). Pineal gland parenchyma in all groups of animals was studied using light optical appliances.

C-Fos protein is one of the triggers for launching the processes of synthesis in the pineal gland under the impact of extreme factors, including stress. Presumably, almost complete absence of c-Fos protein in the pineal gland of osmotic stress-affected rats, which was shown by our experiment, is related to the chronic character of this stress, since the highest content of c-fos gene products is observed 1-2 hours after the impact of stress factors. Chronic stress inhibits the activity of c-fos gene in PVH because of increased content of glucocorticoids in the blood plasma.

Mild but reliable increase in the content of c-Fos protein in pinealocytes in conditions of stress was observed only after intranasal infusion of peptide H-Glu-Asp-Gly-OH (FIG. 3).

Such effect of peptide H-Glu-Asp-Gly-OH was observed only in conditions of stress. This shows that peptide H-Glu-Asp-Gly-OH is involved in peptide self-regulation of pineal gland activity in case of extreme conditions of the organism.

It was found, that c-Fos protein is unevenly distributed among different pinealocytes. Stress enables to identify clusters (consisting of 5-10 cells), containing c-Fos in the cytoplasm. These clusters of pinealocytes may be groups of interacting cells.

The estimation of pineal gland parenchyma status revealed partial reduction of osmotic stress induced dilation of capillaries and pericapillary space by intranasal infusion of H-Glu-Asp-Gly-OH peptide (FIG. 4).

Thus, peptide H-Glu-Asp-Gly-OH exerts an effect on the pineal gland under the impact of extreme factors on the organism. Peptide H-Glu-Asp-Gly-OH inhibits the pathologic changes in the structure of pineal gland parenchyma in case of osmotic stress, and its effect on the pineal gland is mediated by the activation of certain genes.

EXAMPLE 5

Effect of Peptide H-Glu-Asp-Gly-OH on the Activity of Enkephalinases in Human Blood Serum This study was aimed at identifying the opioid activity of peptide H-Glu-Asp-Gly-OH. Opioid activity may be stipulated by both interactions of peptides with different types of opioid receptors and by inhibiting enkephalinases, leading to the corresponding increase in the concentration of native enkephalins.

The ability of peptide H-Glu-Asp-Gly-OH to influence the activity of endogen opioid peptide degradation enzymes, i.e. enkephalins, was estimated in kinetic studies judging by disintegration of low concentrations (0.15 µM) of [$^3$H]Leu-enkephalin by human blood serum enzymes. Commonly used enkephalinase inhibitors N-carboxymethyl-Phe-Leu (N-CMPL) and bacitracin were used as comparison substances. Summary enkephalinase activity of the blood serum taken from 5 healthy donors, was estimated in vitro. Results were evaluated after 4 studies.

FIG. 5 displays the effect of peptide H-Glu-Asp-Gly-OH on enkephalinase activity of human blood serum.

The study revealed, that peptide H-Glu-Asp-Gly-OH, introduced into the cultural medium in the ultimate concentration of 10 µg/ml, inhibited the activity of blood serum enkephalinases (FIG. 5). The degree of inhibition was comparable with that of N-CMPL (10 µg/ml) and bacitracin (50 µg/ml).

It is known, that enzymatic degradation of blood enkephalins takes minutes, and that is why these enzymes are the best to reflect peripheral biological effects of endogen opioid peptides. The application of peptide H-Glu-Asp-Gly-OH, inhibiting the activity of blood serum enkephalinases, is aimed at preserving the regulatory properties of endogen opioid peptides, which provides for its use for correcting stress-induced disorders.

EXAMPLE 6

Study of Peptide H-Glu-Asp-Gly-OH Toxicity

Common toxicity of peptide H-Glu-Asp-Gly-OH was studied according to the requirements stated in the "Manual for experimental (pre-clinical) study of new pharmacological substances" (2000): acute toxicity in case of single administration of the substance, as well as sub-acute and chronic toxicity in case of long-term administration of the peptide.

Acute toxicity was studied on 66 white mongrel male mice with body weight of 20-22 g. The animals were randomly subdivided into 6 equal groups. The substance was administered to the animals once, intramuscularly, in the doses of 1 mg/kg, 2 mg/kg, 3 mg/kg, 4 mg/kg, 5 mg/kg in 0.25 ml of sterile 0.9% NaCl solution. Control animals received 0.9% NaCl solution in the same volume.

Sub-acute toxicity was studied on 64 white mongrel male rats with body weight of 180-220 g. Experimental animals daily, once a day, for 90 days received the substance intramuscularly in the doses of 1 µg/kg, 0.1 mg/kg, 1 mg/kg in 0.5 ml of sterile 0.9% NaCl solution. Control animals received sterile 0.9% NaCl solution in the same volume. Morphological composition and properties of the animals' peripheral blood was studied before the administration of the substance, as well as on the $30^{th}$, $60^{th}$ and $90^{th}$ day after the beginning of the administration of the substance. Biochemical and coagulologic indices of the blood were studied upon completion of the experiment.

The studies of chronic toxicity were conducted for 6 months, basing on the term of recommended clinical administration of the substance, on 92 male guinea pigs with body weight of 310-350 g. Experimental animals received the peptide daily, once a day, intramuscularly, for 6 months in the doses of 1 µg/kg, 0.1 mg/kg, 1 mg/kg in 0.5 ml of sterile 0.9% NaCl solution. Control animals received sterile 0.9% NaCl solution in the same volume and by the same schedule. Traditional methods were used for the evaluation of the following indices of the animals' peripheral blood: the quantity of erythrocytes, hemoglobin, reticulocytes, thrombocytes, leukocytes, leukocyte formula, erythrocyte sedimentation rate (ESR), erythrocyte resistance. Alongside with that, the content of total protein in the serum was identified using Lowry's method, as well as potassium and sodium content using the method of plasma spectrophotometry. After the completion of the experiment pathomorphologic studies of animal brain and spinal cord, spinal cord ganglia, thyroid gland, parathyroid glands, adrenal glands, testis, pituitary gland, heart, lungs, aorta, liver, kidneys, urinary bladder, pancreas, stomach, small intestine, large intestine, thymus, spleen, lymph nodes and bone marrow were performed.

Acute toxicity study revealed, that a single administration of the studied peptide to animals in the dose, which exceeds the therapeutic one, recommended for clinical administration, by more than 5000 times, does not cause toxic reactions, which points out a wide range of therapeutic application of the substance.

The study of sub-acute and chronic toxicity of the peptide points out the absence of side effects in case of long-term administration of the substance in doses, which exceed the therapeutic one by 100-1000 times. The study of the peptide effect on the morphological composition of guinea pigs' blood revealed an increase in the quantity of leukocytes 3 months after the beginning of the administration of the substance. This index was normalized by the $6^{th}$ month of the observation (see Table). All other indices of the morphological composition of animals' blood remained largely unchanged. No reliable effect of the substance on ESR, erythrocyte resistance and biochemical indices of the blood serum was revealed.

The evaluation of general status of the animals, of morphological and biochemical indices of the peripheral blood, of morphological status of internal organs, of the status of cardiovascular and respiratory systems, as well as of the functions of the liver and kidneys did not reveal any pathologic changes in the organism.

The absence of common toxicity allows to recommend the pharmaceutical composition, containing peptide H-Glu-Asp-Gly-OH as its active base, for clinical studies.

EXAMPLE 7

Effect of Peptide H-Glu-Asp-Gly-OH on Human Functional Status Under the Effect of Low Oxygen Partial Pressure Effect of peptide H-Glu-Asp-Gly-OH on human functional status and working ability in extreme conditions under the effect of low oxygen partial pressure was studied by examining 80 healthy men aged 20-22 years. The participants of the study were subdivided into 3 groups: 20 men formed the control group, while main groups I and II consisted of 30 persons each. Background study, including the examination of respiratory, cardiovascular and central nervous systems was performed on the first day of the experiment.

After the completion of background study the members of main group I began receiving the pharmaceutical composition, containing peptide H-Glu-Asp-Gly-OH as its active base, by intranasal infusions, in the dose of 5.0 mg in 1 ml of physiological solution (subgroup I), in the dose of 100.0 µg (subgroup II) and in the dose of 1.0 µg in 1.0 ml of physiological solution (subgroup III) 3 times a day, for 2 days. Thus, the members of main group I received the peptide H-Glu-Asp-Gly-OH intranasally in the dose of 10 mg (subgroup I), 200 µg (subgroup II) and 2 µg (subgroup III) per course.

Members of main group II began receiving the pharmaceutical composition, containing the peptide H-Glu-Asp-Gly-OH as its active base, after the completion of background study, intramuscularly, in the dose of 5.0 mg in 1 ml of physiological solution (subgroup I), in the dose of 100.0 µg (subgroup II) and in the dose of 1.0 µg in 1.0 ml of physiological solution (subgroup III) daily, once a day, for 2 days.

Members of the control group received placebo in the form water for injections.

On the $4^{th}$ day of the experiment the members of all 3 groups were subjected to the effect of hypoxic hypoxia by "rising" them to the altitude of 5000 meters for 60 minutes of exposition without auxiliary oxygen supply, which was imitated using the pressure chamber SBK-80. Participants of the experiment were shortly examined before the beginning of the "rise", during the experiment and after its completion. On the $5^{th}$ day of the experiment all participants were subjected to a full scale final examination. During the study reactive anxiety in all participants was on the moderate level (31-45 points). However, differently directed dynamics of this index were observed in different groups within this level. After 2 days of administration of the pharmaceutical composition containing peptide H-Glu-Asp-Gly-OH in different doses as its active base reactive anxiety in participants of the experiment was reduced by 10-13% depending on the dosage and method of administration of the pharmaceutical composition as compared to the members of the control group. On the next day after the impact of hypoxia the control group, which received placebo, showed 9-10% increase in reactive anxiety as compared to the initial level, while those participants, who received the pharmaceutical composition containing peptide H-Glu-Asp-Gly-OH in different doses as its active base showed the level of this index equal to the initial one independently of the method of administration. Similar dynamics were observed in the results of "SAN" test ("state of health, activity, mood").

Hypoxic hypoxia worsened the subjective status in all three groups, but to a different extent. Persons, who had received the pharmaceutical composition, containing peptide H-Glu-Asp-Gly-OH as its active base, reported their subjective status equal to the initial level in case of intramuscular administration of the peptide in different doses, or 4-5% decrease in the subjective status in case of intranasal infusion. Placebo group showed 10-15% decrease in the subjective status. On the next day after the impact of hypoxia the subjective status of study participants treated with the pharmaceutical composition containing peptide H-Glu-Asp-Gly-OH as its active base was better than the initial level by 15% in case of intramuscular administration or by 10% in case of intranasal infusion, while the placebo group showed this index being 4-5% worse than the initial level. It is noteworthy, that the most stabile indices were registered in persons, who received the studied composition in the dose of 5.0 mg, both by intramuscular injection and intranasal infusion.

The obtained data show, that peptide H-Glu-Asp-Gly-OH exerts a noticeable effect on the subjective status of experiment participants by reducing the emotional and behavioral manifestations of stress, decreasing anxiety, enhancing activity, improving the status and the mood. It was objectively shown, that study participants, who received the pharmaceutical composition containing peptide H-Glu-Asp-Gly-OH as its active base in different doses, both intramuscularly and intranasally, were more tolerant to hypoxic hypoxia. Good tolerability to hypoxia was shown by 80-90% of study participants, who received peptide H-Glu-Asp-Gly-OH and only by 60% of placebo group members.

Heart rate (HR) dynamics was similar in all groups. Hypoxia caused a reliable increase in HR: study participants, who received the pharmaceutical composition containing peptide H-Glu-Asp-Gly-OH as its active base, showed 10-20% increase in this index, depending on the dose and method of administration, while placebo group members showed a 30-40% increase. After the completion of hypoxic test the groups treated with the pharmaceutical composition containing peptide H-Glu-Asp-Gly-OH as its active base showed HR levels similar to the initial ones, while placebo group showed HR levels 6-7% higher than the initial ones. Systolic arterial pressure returned to the initial level by the $10^{th}$-$15^{th}$ minute of experiment in the groups treated with the pharmaceutical composition containing peptide H-Glu-Asp-Gly-OH as its active base, while the placebo group recovered its initial pressure only after the end of hypoxic test.

Diastolic arterial pressure dynamics in study participants were similar: a rise during the first 10 minutes of the hypoxic test, and then a gradual decrease. Physical working capacity was higher in the end of the test in all groups, but it was increased to different extents. So, physical working capacity index (PWC 170) and the maximum oxygen consumption in study participants treated with the pharmaceutical composition containing peptide H-Glu-Asp-Gly-OH as its active base were increased by 15-20% depending on the dosage and the method of administration, while the placebo group showed the increase in these indices only by 10-11%. A distinctive feature of peptide H-Glu-Asp-Gly-OH effect consisted in reduced lung ventilation in case of dosed physical load after hypoxia impact.

Provided data show, that the functional status during hypoxic test was more physiologically adequate in the groups treated with the pharmaceutical composition containing peptide H-Glu-Asp-Gly-OH in different doses, than in the placebo group.

Thus, the study of peptide H-Glu-Asp-Gly-OH efficiency in human volunteers subjected to a pressure chamber "rise" to the altitude of 5000 meters without auxiliary oxygen supply showed, that study participants, who received the pharmaceutical composition containing peptide H-Glu-Asp-Gly-OH as its active base revealed a better tolerance to hypoxia impact, both objectively and subjectively. Revealed dose-dependent effect enables to recommend the application of the studied pharmaceutical composition in the doses from 5 mg to 1 µg in 1 ml of physiological solution, both intramuscularly and intranasally, depending on the extent of functional status disorders in study participants.

Fluctuations of physiological indices were smoother in the group of study participants treated with the pharmaceutical composition containing peptide H-Glu-Asp-Gly-OH as its active base. Besides, these indices were sooner restored to the background values in this group, which points out the stress protective properties of peptide H-Glu-Asp-Gly-OH.

TABLE

| | Administration of peptide H-Glu-Asp-Gly-OH (1 µg/kg) | | | |
| --- | --- | --- | --- | --- |
| | 3 months | | 6 months | |
| Index | Control (n = 24) | Peptide (n = 24) | Control (n = 24) | Peptide (n = 24) |
| Erythrocytes, $\times 10^{12}$/l | 5.3 ± 0.6 | 5.2 ± 0.1 | 5.4 ± 0.3 | 5.2 ± 0.7 |
| Hemoglobin, g/l | 14.2 ± 1.4 | 14.4 ± 0.9 | 14.5 ± 1.3 | 14.8 ± 1.1 |
| Reticulocytes, % | 1.3 ± 0.07 | 1.1 ± 0.08 | 1.1 ± 0.05 | 1.2 ± 0.04 |
| Thrombocytes, $\times 10^{9}$/l | 143.7 ± 7.9 | 143.1 ± 4.5 | 144.5 ± 8.6 | 142.8 ± 6.2 |
| Leukocytes, $\times 10^{9}$/l | 9.4 ± 0.5 | 11.8 ± 0.2* | 9.6 ± 0.5 | 10.3 ± 0.6 |
| Stab neutrophils, % | 0.31 ± 0.04 | 0.30 ± 0.02 | 0.33 ± 0.04 | 0.35 ± 0.01 |
| Segmented neutrophils, % | 45.8 ± 2.1 | 43.9 ± 1.8 | 46.2 ± 3.5 | 45.4 ± 3.0 |
| Eosinophils, % | 0.69 ± 0.05 | 0.67 ± 0.06 | 0.72 ± 0.04 | 0.73 ± 0.04 |
| Basophils, % | 0.61 ± 0.04 | 0.63 ± 0.03 | 0.72 ± 0.03 | 0.65 ± 0.08 |
| Monocytes, % | 2.5 ± 0.02 | 2.6 ± 0.01 | 2.6 ± 0.06 | 2.4 ± 0.04 |

TABLE-continued

| | Administration of peptide H-Glu-Asp-Gly-OH (1 μg/kg) | | | |
| --- | --- | --- | --- | --- |
| | 3 months | | 6 months | |
| Index | Control (n = 24) | Peptide (n = 24) | Control (n = 24) | Peptide (n = 24) |
| Lymphocytes, % | 48.9 ± 2.5 | 51.3 ± 2.2 | 51.3 ± 2.7 | 49.7 ± 1.9 |
| ESR, mm/hour | 1.69 ± 0.05 | 1.98 ± 0.09 | 2.01 ± 0.05 | 1.85 ± 0.06 |
| Erythrocyte resistance, % NaCl | | | | |
| maximum | 0.41 ± 0.02 | 0.42 ± 0.02 | 0.42 ± 0.04 | 0.43 ± 0.02 |
| minimum | 0.32 ± 0.05 | 0.31 ± 0.01 | 0.34 ± 0.04 | 0.33 ± 0.06 |
| Total protein in the blood serum, g/l | 72.9 ± 3.1 | 73.6 ± 2.8 | 73.1 ± 3.4 | 72.3 ± 2.9 |
| Sodium in the blood serum, mmole/l | 153.9 ± 5.7 | 155.6 ± 4.7 | 155.5 ± 6.2 | 155.2 ± 4.9 |
| Potassium in the blood serum, mmole/l | 5.1 ± 2.3 | 5.3 ± 2.0 | 5.2 ± 2.1 | 5.1 ± 2.5 |

*P < 0.05 as compared to the control.

The invention claimed is:

1. A pharmaceutical composition consisting of the peptide H-Glu-Asp-Gly-OH and a pharmaceutically acceptable carrier.

2. A pharmaceutical composition comprising the peptide H-Glu-Asp-Gly-OH and a pharmaceutically acceptable carrier, which is a parenteral or intranasal formulation.

3. A method of treating a patient for a stress induced disorder caused by osmotic stress, wherein the method consists of administering to the patient a pharmaceutical composition according to claim 1 having the peptide in a dose of 0.01-100 μg/kg of body weight at least once a day during a period necessary for attaining a therapeutic effect in the patient.

4. The method according to claim 3, wherein the composition is administered parenterally or by intranasal infusion.

5. An intranasal formulation comprising the peptide H-Glu-Asp-Gly-OH and a pharmaceutically acceptable carrier.

6. The pharmaceutical composition of claim 1, which is a parenteral formulation.

7. The pharmaceutical composition of claim 1, which is an intranasal, formulation.

8. The pharmaceutical composition of claim 2, which is a parenteral formulation.

9. The pharmaceutical composition of claim 2, which is an intranasal formulation.

10. The pharmaceutical composition of claim 2, wherein the pharmaceutical carrier is physiological saline or sterile water.

11. A method of modulating the content of biogen amines in the brain cortex and/or the blood serum of a patient in need thereof, which method consists of administering to the patient a pharmaceutical composition according to claim 1 having the peptide in a dose of 0.01-100 μg/kg of body weight at least once a day during a period necessary for attaining a modulating effect on the content of biogen amines in the brain cortex and/or the blood serum of the patient.

12. A method of increasing the level of c-fos gene expression in the neuronal cells of a patient under stress due to motional restriction, which method consists of administering to the patient a pharmaceutical composition according to claim 1 having the peptide in a dose of 0.01-100 μg/kg of body weight at least once a day during a period necessary for attaining an increase in the level of c-fos gene expression in the neuronal cells of the patient.

13. A method of reducing the level of an enkephalinase in the serum of a patient in need thereof, which method consists of administering to the patient a pharmaceutical composition according to claim 1 having the peptide in a dose of 0.01-100

µg/kg of body weight at least once a day during a period necessary for attaining a reduced level of an enkephalinase in the serum of the patient.

14. A method of treating a patient for hypoxic hypoxia, which method consists of administering to the patient a pharmaceutical composition according to claim 1 having the peptide in a dose of 0.01-100 µg/kg of body weight at least once a day during a period necessary for reducing the hypoxic hypoxia in the patient.

* * * * *